US00PP16763P2

(12) United States Plant Patent
Austin

(10) Patent No.: US PP16,763 P2
(45) Date of Patent: Jul. 4, 2006

(54) SHRUB ROSE PLANT NAMED 'AUSINTENSE'

(50) Latin Name: *Rosa hybrida*
Varietal Denomination: AUSintense

(75) Inventor: David C. H. Austin, Wolverhampton (GB)

(73) Assignee: David Austin Roses, Ltd., Albrighton (GB)

( * ) Notice: Subject to any disclaimer, the term of this patent is extended or adjusted under 35 U.S.C. 154(b) by 34 days.

(21) Appl. No.: 11/034,317

(22) Filed: Jan. 11, 2005

(51) Int. Cl.
*A01H 5/00* (2006.01)

(52) U.S. Cl. ..... Plt./107

(58) Field of Classification Search ..... Plt./107, Plt./102, 149
See application file for complete search history.

*Primary Examiner*—Anne Marie Grunberg
*Assistant Examiner*—June Hwu
(74) *Attorney, Agent, or Firm*—Klarquist Sparkman LLP

(57) ABSTRACT

Shrub rose plant having large, cupped blooms of dark pink having a fruity fragrance with Old Rose and shiny foliage on arching growth.

1 Drawing Sheet

Genus and species: *Rosa hybrida.*
Variety denomination:'AUSintense'.

ORIGIN OF THE INVENTION

The present invention relates to a new and distinct variety of a shrub rose plant named 'AUSintense' which was originated by me by crossing an unnamed, unpatented seedling with the variety 'AUSgold' (Golden Celebration), U.S. Plant Pat. No. 8,688.

BACKGROUND OF THE INVENTION

The primary objective of this breeding was to produce a very free-flowering, healthy rose plant with dark pink blooms on a bushy, branching shrub.

BRIEF SUMMARY OF THE INVENTION

The objective was substantially achieved, along with other desirable improvements, as evidenced by the following unique combination of characteristics that are outstanding in the new variety and that distinguish it from its parents, as well as from all other varieties of which I am aware:

1. Large cupped blooms of deep pink.
2. Fruity fragrance with Old Rose.
3. Shiny foliage on arching growth.

Asexual reproduction of this new variety by budding, as performed at Albrighton, England, shows that the foregoing and all other characteristics and distinctions come true to form and are established and transmitted through succeeding propagations.

Comparison with Parents

'AUSintense' has dark pink blooms on a taller shrub as compared with the apricot blooms of the unnamed seedling. 'AUSintense' has a fruit and Old Rose fragrance as compared to 'AUSgold' (U.S. Plant Pat. No. 8,688) which has yellow blooms with a tea fragrance.

Comparison with Similar Variety

'AUSintense' has rich, shiny green foliage and dark pink, large-cupped blooms as compared to 'AUSguard' (unpatented) which has paler foliage and shallow-cupped, paler blooms.

BRIEF DESCRIPTION OF THE ILLUSTRATION

The accompanying illustration shows typical specimens of the vegetative growth and flowers of this new variety in different stages of development, depicted in color as nearly true as it is reasonably possible to make the same in a color illustration of this character.

DETAILED BOTANICAL DESCRIPTION

The following is a detailed description of my new rose cultivar with color descriptions using terminology in accordance with The Royal Horticultural Society (London) Colour Chart (2001), except where ordinary dictionary significance of color is indicated.

Parentage:
*Seed parent.*—Unnamed Seedling. (Unpatented).
*Pollen parent.*—'AUSgold' (U.S. Plant Pat. No. 8,688).

FLOWER

Observations made from plants commencing at one year of age grown in a garden environment at Albrighton, England.

Blooming habit: Recurrent. The number of blooms per plant during the growing season is profuse, but there are too many to count.

Bud:
*Size.*—About 3 cm long and 2.5 cm in diameter when the petals start to unfurl.
*Form.*—The bud form is pointed globular.
*Color.*—When sepals first divide, bud color is Red Group 53C. When half blown, the upper sides of the petals are Red-Purple Group 61C; and the lower sides of the petals are Red-Purple Group 60D.

*Sepals*.—Color: Upper surface: Yellow-Green Group 147D. Lower surface: Yellow-Green Group 144C. Length: 2.5 cm. Width: 0.8 cm. Shape: Ovate. Surface texture: Upper surface: Pubescent. Lower surface: Slightly rough. There are three normally appendaged sepals. There are two unappendaged sepals with canescent and glandular edges.

*Receptacles*.—Color: Irregular patches of Green Group 143C and Greyed-Purple Group 187A. Shape: Campanulate. Size: Medium, about 1 cm long×0.7 cm wide. Surface: Smooth.

*Peduncle* .—Length: Medium, averaging about 8 cm. Surface: Prickly. Color: Greyed-Red Group 178A. Strength: Weak.

Bloom:

*Size*.—Large. Average open diameter is about 8.9 cm.

*Borne*.—Several together in rounded clusters of four to seven blooms.

*Stems*.—Strength: Normal. Average length is about 41 cm with a diameter of 0.5 cm.

*Form*.—When first open: Cupped. Permanence: Outer petal edges curl slightly.

*Petalage*.—Number of petals under normal conditions: 100–110.

*Color*.—The upper sides of the petals are Red-Purple Group 61C. The reverse sides of the petals are Red-Purple Group 61C. The base of each petal is Yellow Group 4A. The major color on the upper side is Red-Purple Group 61C.

*Variegations*.—None.

*Discoloration*.—The general tonality at the end of the first day: Red-Purple Group 64C. At the end of the third day: Red-Purple Group N74C.

*Fragrance*.—Strong, fruit and Old Rose.

Petals:

*Texture*.—Thick and leathery.

*Size*.—Width: 2.8 cm. Length: 3.8 cm.

*Surface*.—Smooth.

*Shape*.—Narrow elliptical. Margin: Incurved with very weak undulation. Apex Shape: Emarginate. Base Shape: Cuneate. Form: Incurved.

*Arrangement*.—Quartered.

*Petaloids*.—Number: Four. Color: Red-Purple Group 61C.

*Persistence*.—Petals hang on and dry.

*Lastingness*.—On the plant: Fair (about 4–5 days). As a cut flower: Fair (about 3–4 days).

Reproductive Parts:

*Stamens*.—Number: 51. Length: 9 mm. Anthers: Length: 2 mm. Color: Yellow-Orange Group 15B. Arrangement: Mixed with Petaloids. Filaments: Color: Yellow-Orange Group 16B. Length: 7 mm. Pollen: Color: Yellow-Orange Group 15B.

*Pistils*.—Number: 61. Length: 10 mm. Styles: Color: Yellow Group 2D. Length: 9 mm. Stigmas: Color: Green-Yellow Group 1A. Length: 1 mm.

*Hips*.—None observed.

PLANT

*Form*.—Shrub.

*Growth*.—Branching and vigorous.

*Age at maturity*.—Two years.

*Mature plant*.—Height: 1.2 m. Width: 1 m.

*Wood*.—Mature Stem: Average length: 40 cm. Average diameter: 7 mm. Internode distance: 5 cm. The above measurements are all variable, depending on growing conditions in a season.

*Rootstock*.—Dr. Huey in the United States. *Rosa dumetorum* 'Laxa' for the observed plants in the United Kingdom.

Foliage: Number of leaflets on normal mid-stem leaves: 5.

*Size*.—Large. About 13.9 cm long×9.7 cm wide.

*Quantity*.—Normal. Average number leaves per flowering stem: 10.

*Color*.—New foliage: Upper side. Yellow-Green Group 146A. Lower side: Yellow-Green Group 146B. Old foliage: Upper side: Yellow-Green Group 147A. Lower side: Yellow-Green Group 147B.

Leaflets:

*Size*.—About 5.5 cm long×3.4 cm wide.

*Shape*.—Ovate.

*Base shape*.—Obtuse.

*Apex shape*.—Acuminate.

*Texture*.—Upper Side: Leathery.

*Edge*.—Serrated.

*Serrations*.—Double and small.

*Petiole*.—Color: Yellow-Green Group 144C.

*Petiole rachis*.—Color: Yellow-Green Group 144C. Underside: Prickles.

*Auricle shape*.—Subulate.

*Stipules*.—Length: 2.7 cm: serrated.

*Disease resistance*.—Resistant to downy and powdery mildews, blackspot and rust under normal growing conditions.

*Pest resistance*.—Not tested.

*Vein color*.—Yellow-Green Group 154D.

*Venation pattern*.—Reticulate.

Wood:

*New wood*.—Color: Greyed-Orange Group 166A. Bark: Smooth.

*Old wood*.—Color: Yellow-Green Group 146A. Bark: Smooth.

Prickles:

*Quantity*.—On main canes from base: Ordinary, 17 per 30 cm per stem length. On laterals from main canes: Ordinary, 31 per 30 cm per stem length.

*Foam*.—Hooked downward.

*Length*.—5–9 mm.

*Color when young*.—Greyed-Purple Group 187B.

*Color when mature*.—Greyed-Brown Group 199C.

Small prickles:

*Quantity*.—On main stalks: None. On laterals: None.

Winter hardiness: Not tested.

I claim:

1. A new and distinct variety of rose plant of the shrub class, substantially as herein shown and described, characterized particularly by its large, cupped blooms of dark pink having a fruity fragrance with Old Rose and shiny foliage on arching growth.

* * * * *

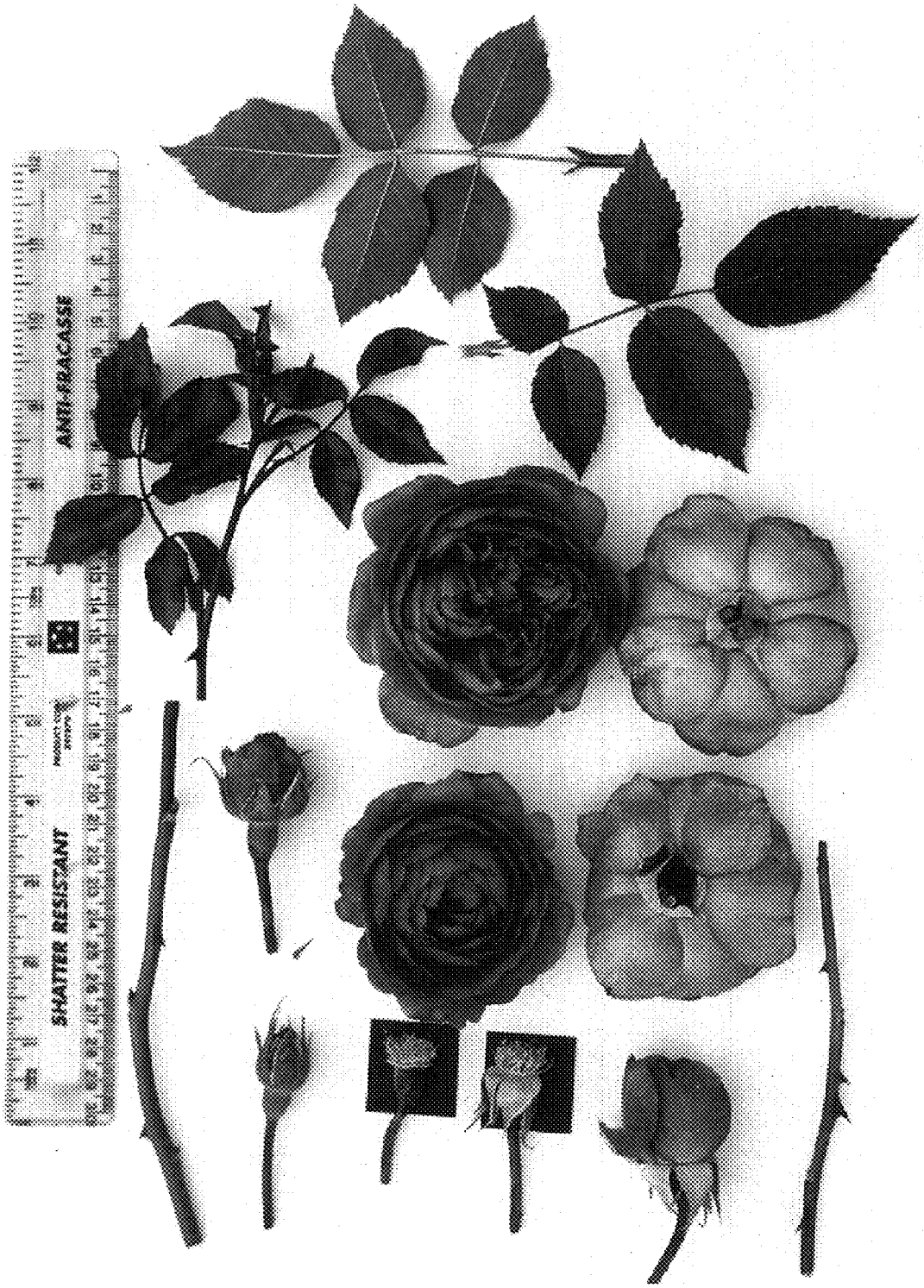
SHATTER RESISTANT
ANTI-FRACASSE